United States Patent [19]

Thibault

[11] 4,436,549

[45] Mar. 13, 1984

[54] THIADIAZINE HERBICIDES

[75] Inventor: Thomas D. Thibault, Indianapolis, Ind.

[73] Assignee: Eli Lilly and Company, Indianapolis, Ind.

[21] Appl. No.: 437,380

[22] Filed: Oct. 28, 1982

[51] Int. Cl.³ .................... A01N 43/88; C07D 285/16
[52] U.S. Cl. ............................................ 71/90; 544/8
[58] Field of Search ................................ 544/8; 71/90

[56] References Cited

U.S. PATENT DOCUMENTS

| | | | |
|---|---|---|---|
| 3,779,736 | 12/1973 | Doyle, Jr. | 71/90 |
| 3,862,183 | 1/1975 | Doyle, Jr. | 260/243 |
| 4,254,259 | 3/1981 | Campaigne et al. | 544/8 |
| 4,271,166 | 6/1981 | Ward | 424/263 |

*Primary Examiner*—John M. Ford
*Attorney, Agent, or Firm*—Kathleen R. S. Page; Arthur R. Whale

[57] ABSTRACT

N-(1,3,4-Thiadiazin-2-yl)-2,6-dialkoxybenzamide derivatives useful as herbicides.

15 Claims, No Drawings

THIADIAZINE HERBICIDES

SUMMARY OF THE INVENTION

The present invention relates to a compound of the formula

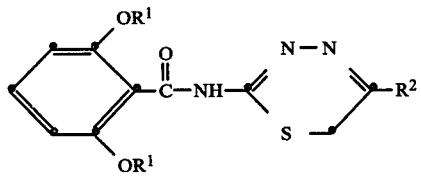

wherein:
each $R^1$ is independently methyl or ethyl;
$R^2$ is $C_1$–$C_{10}$ alkyl, $C_3$–$C_8$ cycloalkyl or $C_1$–$C_4$ alkyl substituted $C_3$–$C_8$ cycloalkyl;
and the agronomically-acceptable salts thereof.

The present invention also provides a herbicidal method for the use of such novel compounds, as well as compositions containing such compounds.

DETAILED DESCRIPTION OF THE INVENTION

In the above formula, $C_1$–$C_{10}$ alkyl includes methyl, ethyl, n-propyl, isopropyl, n-butyl, sec.-butyl, isobutyl, t-butyl, n-pentyl, isopentyl, sec.-pentyl, neopentyl, n-hexyl, sec.-hexyl, isohexyl, 1-ethyl-1-methylpropyl, n-heptyl, isoheptyl, sec.-heptyl, 1,1-diethylpropyl, n-octyl, sec.-octyl, isooctyl, n-nonyl, sec.-nonyl, isononyl, n-decyl, sec.-decyl, and the like. $C_4$–$C_{10}$ Alkyl is preferred.

$C_3$–$C_8$ Cycloalkyl represents saturated monocyclic cycloalkyl groups such as cyclopropyl, cyclobutyl, cyclopentyl, cyclohexyl, cycloheptyl, and cyclooctyl.

The term "$C_1$–$C_4$ alkyl substituted $C_3$–$C_8$ cycloalkyl" represents a $C_3$–$C_8$ cycloalkyl group bearing only one $C_1$–$C_4$ alkyl substituent. Such $C_1$–$C_4$ alkyl substituted $C_3$–$C_8$ cycloalkyl groups include 2-methylcyclopropyl, 2-isopropylcyclopropyl, 2-t-butylcyclopropyl, 2-ethylcyclobutyl, 2-sec.-butylcyclopentyl, 1-methylcyclopentyl, 1-ethylcyclopentyl, 1-methylcyclohexyl, 1-ethylcyclohexyl, and the like.

The compounds of the present invention are prepared by procedures well known to those skilled in the art of agricultural organic chemistry. The preferred process involves the acylation of a substituted-1,3,4-thiadiazine amine with an appropriately substituted benzoic acid derivative to provide the corresponding benzamide according to the following reaction scheme:

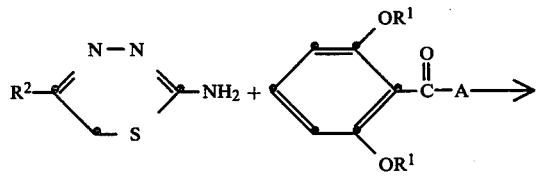

-continued

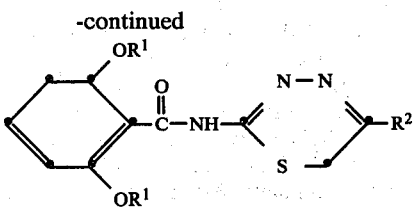

wherein $R^1$ and $R^2$ are as defined above and A is a good leaving group such as halogen, an activated ester forming group such as 4-nitrophenoxy

($C_1$–$C_4$ alkyl) and the like.

The preferred synthetic procedure involves the above scheme wherein A is halogen, most preferably chlorine or bromine. This reaction can be carried out by combining the benzoic acid derivative with about an equimolar quantity of the thiadiazine amine in a mutual solvent such as tetrahydrofuran, diethyl ether, dichloromethane, dioxane, dimethylsulfoxide, dimethylformamide, benzene, toluene, and the like. If desired, a base can be utilized in the acylation reaction to act as an acid scavenger. Commonly used bases include sodium carbonate, sodium hydride, potassium carbonate, sodium hydroxide, pyridine, triethylamine and related bases. Bases such as pyridine act as their own solvent and need no additional solvent. the acylation generally is substantially complete after about two to about ninety hours when carried out at a temperature of about 20° to about 200° C., preferably from about 30° to about 120° C. The product of the reaction, an N-thiadiazine benzamide of the invention, can be isolated by simply removing the reaction solvent, for instance by evaporation under reduced pressure. Also, the reaction mixture may be added to water and the product collected by filtration or extracted into a water immiscible solvent. The product can be further purified if needed by any of several routine methods, including crystallization, from solvents such as ethanol, ethyl acetate, diethyl ether, toluene, or the like; chromatography over solid supports such as silica or alumina, and related purification techniques.

An alternative method for preparing the thiadiazine benzamides of this invention comprises the direct coupling of a 2,6-dialkoxybenzoic acid with a thiadiazine amine. Such coupling reaction necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The direct coupling of a benzoic acid and a thiadiazine amine is carried out by combining about equimolar quantities of the starting materials in the presence of an equimolar quantity or slight excess of coupling reagent. The reaction generally is carried out in an unreactive organic solvent such as dichloromethane or dimethylformamide, and usually is complete within about twenty-four hours when conducted at a temperature of about 0° to about 30° C. The benzamide product is readily isolated and purified by standard procedures.

A further embodiment of the present invention are the agronomically-acceptable salts of the benzamides defined by the above general formula. Such salts may be particularly preferred when it is desired to increase the water solubility of the benzamides, since the agronomically-acceptable salts are in general highly soluble in water and similar polar solvents. Typical salts provided herein are prepared by reaction of a benzamide with a strong base such as sodium hydride, lithium hydride or potassium hydride, generally in a solvent such as diethyl ether or the like. Sodium salts are preferred salt forms for the benzamides of this invention. All of the alkali metal salts are agronomically-acceptable.

The preparation of the benzamides of this invention requires the use of starting materials which are either known or are readily preparable by methods familiar to those in the art. Most of the substituted benzoic acids which are required are commercially available. The reactive derivatives of such benzoic acids are prepared by routine procedures. For example, a preferred synthetic method according to this invention requires the use of substituted benzoic acid halides. These compounds are prepared by the reaction of a benzoic acid with a halogenating agent such as oxalyl chloride, thionyl chloride, phosphorus trichloride or phosphorus tribromide.

The following detailed examples are provided in an effort to more fully illustrate specific aspects of this invention. The examples are not intended to be limiting in any respect and should not be so construed.

EXAMPLE 1

N-[5-(1,1-Dimethylethyl)-6H-1,3,4-thiadiazin-2-yl]-2,6-dimethoxybenzamide

A. 1-Bromo-3,3-dimethyl-2-butanone

To a stirred solution of 50.0 g of 3,3-dimethyl-2-butanone dissolved in 400 ml diethyl ether cooled to approximately 0°–5° C. with an ice bath was added 79.8 g of bromine over a 45-minute period. A catalytic amount of aluminum chloride was added to the reaction mixture. When the addition was complete, the mixture was stirred for 20 minutes and washed first by water and next by a saturated sodium bicarbonate solution. The organic phase was separated, dried over anhydrous sodium sulfate and evaporated under reduced pressure. The resulting residue was used directly in the following procedure.

B. 2-Amino-5-(1,1-dimethylethyl)-6H-1,3,4-thiadiazine

To a suspension of 14.4 g of thiosemicarbazide in 50 ml of ethanol was added 13.6 ml of concentrated hydrochloric acid and 26.8 g of 1-bromo-3,3-dimethyl-2-butanone. The mixture was stirred at reflux overnight, cooled and concentrated under vacuum. The residue was treated with a minimum amount of ethanol. The precipitate was collected by filtration and washed with ethyl acetate and diethyl ether to provide 16.3 g of solid. The solid was dissolved in water, filtered and the pH of the filtrate was raised to approximately 7. This solution was again filtered, and the pH of the filtrate was raised to approximately 10 and cooled. The precipitated solid was collected by filtration to afford 5.83 g of 2-amino-5-(1,1-dimethylethyl)-6H-1,3,4-thiadiazine. mp=75°–77° C.

C. To a solution of 1.71 g of 2-amino-5-(1,1-dimethylethyl)-6H-1,3,4-thiadiazine and 1.01 g triethylamine in 18 ml dioxane was added 2.11 g of 2,6-dimethoxybenzoyl chloride. The reaction mixture was stirred at room temperature for 3 hours and poured into 100 ml water. The solid was collected and recrystallized from ethanol. The second crop of material provided 0.43 g of N-[5-(1,1-dimethylethyl)-6H-1,3,4-thiadiazin-2-yl]-2,6-dimethoxybenzamide. mp=175°–177° C.

Analysis calculated for $C_{16}H_{21}N_3O_3S$: Theory: C, 57.31; H, 6.27; N, 12.54; S, 9.55; Found: C, 56.98; H, 6.03; N, 12.14; S, 9.28.

EXAMPLE 2

N-[5-(1-Ethyl-1-methylpropyl)-6H-1,3,4-thiadiazin-2-yl]-2,6-dimethoxybenzamide

A. 1-Bromo-3-methyl-3-ethyl-2-pentanone

To a solution of 9.0 g of 3-methyl-3-ethyl-2-pentanone in 100 ml diethyl ether cooled to about 0°–5° C. with an ice bath was added 3.6 ml bromine. The reaction mixture was allowed to warm to room temperature and a catalytic amount of aluminum chloride was added. The mixture was stirred for 30 minutes and washed with water and a saturated sodium bicarbonate solution. The organic phase was separated, dried over anhydrous sodium sulfate and evaporated under vacuum to provide an oil. The oil was distilled under vacuum to provide 6.3 g of product. bp=100°–114° C. at 16 mm.

B. 2-Amino-5-(1-ethyl-1-methylpropyl)-6H-1,3,4-thiadiazine

To a suspension of 35.6 g of thiosemicarbazide in 185 ml ethanol was added 33.6 ml of concentrated hydrochloric acid and 78.0 g of 1-bromo-3-methyl-3-ethyl-2-pentanone. The reaction mixture was refluxed overnight and filtered hot. After the filtrate had cooled, the precipitated solid was collected, and washed with cold ethanol and diethyl ether to provide 34.0 g of the hydrochloride salt of the product. m.p.=216°–219° C. The salt was dissolved in hot water and the pH of the aqueous solution was raised to about 10 with concentrated ammonium hydroxide. The precipitate was collected by filtration to provide 21.4 g of 2-amino-5-(1-ethyl-1-methylpropyl)-6H-1,3,4-thiadiazine as a solid.

C. Two grams of 2,6-dimethoxybenzoyl chloride dissolved in about 3 ml dichloromethane was added dropwise to a stirring solution of 1.99 g of 2-amino-5-(1-ethyl-1-methylpropyl)-6H-1,3,4-thiadiazine in 10 ml of pyridine. The mixture was stirred at room temperature for approximately 72 hours and poured into water. The product was extracted into ether and washed with water. The ether phase was dried over anhydrous magnesium sulfate, filtered and evaporated under reduced pressure. The resulting oil was chromatographed over silica gel eluting with a 1:4 (v:v) mixture of ethyl acetate/toluene. Fractions containing the major component were combined and the solvent was evaporated therefrom to afford 0.15 g of N-[5-(1-ethyl-1-methylpropyl)-6H-1,3,4-thiadiazin-2-yl]-2,6-dimethoxybenzamide. mp=134°–140° C.

Analysis calculated for $C_{18}H_{25}N_3O_3S$; Theory: C, 59.50; H, 6.89; N, 11.57; Found: C, 59.43; H, 6.69; N, 11.31.

The novel compounds of the present invention have been found to display useful pre- and postemergent herbicidal activity against a variety of weed species. The compounds may be applied directly to the plants when young, but are preferably applied to the soil prior to the emergence of the plant. The compounds may be either incorporated into the soil, by using a conventional disc or harrow prior to planting the seeds of the desired crop species, or by surface applying the compound to the soil surface before plant emergence. In this latter procedure the compounds are merely permitted to leach into the soil with the assistance of rainfall, for example. While the compounds of the present invention display activity against a wide variety of weed species, they are most effective against lambsquarter, pigweed, mustard, jimsonweed and morningglory.

It is therefore provided as another aspect of the present invention a method for controlling undesired plants which comprises applying to the plants a growth inhibiting amount of a compound of the invention.

The term "growth inhibiting amount", as defined herein, refers to an amount of a compound of the present invention which either kills or stunts the growth of the weed species for which control is desired. This amount will generally be from about 0.05 to about 15.0 pounds of the compound per acre (about 0.056 to about 16.8 kg/ha). The compounds are more preferably applied at rates of about 0.25 to about 8.0 pounds per acre (about 0.28 to about 8.96 kg/ha). The exact concentration of compound required varies with the weed species to be controlled, type of formulation, soil type, climate conditions and the like.

The term "undesired plants", as defined herein, refers to both weeds and weed seeds which are present at the location to be treated with a compound of the present invention. The compounds can be applied to the soil to selectively control undesired plants by soil contact when the weed seeds are germinating and emerging. They can also be used directly to kill emerged weeds by direct contact with the exposed portion of the weed.

The compounds of the present invention may also be formulated with a suitable agriculturally-acceptable carrier. Such compositions will contain from about 0.1 to about 95.0 percent by weight of the active ingredient, depending on the composition desired. Sprayable formulations are preferred, because of the rapidity and economy of application.

The most convenient formulations are in the form of concentrated compositions to be applied by spraying as water dispersions or emulsions containing in the range from about 0.1 percent to about 10 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 5 percent to about 10 percent by weight of the wettable powder, are chosen from among the sulfonated lignins, the condensed napthalenesulfonates, the alkyl sulfates and the like.

A typical emulsifiable concentrate comprises from about 0.1 to about 6 pounds of a compound of the invention per gallon of liquid, dissolved in a mixture of organic solvents and emulsifiers. The organic solvent is typically chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

Dust compositions containing a compound of the present invention usually contain from about 0.1 to about 10 percent of the compound. Dusts are prepared by intimately mixing and finely grinding the compound with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil. Granules comprise a compound of the invention dispersed on a granular inert carrier such as coarsely ground clay of from about 0.1 to about 3 mm particle size, and will contain the active ingredient at a concentration of from about 0.1 percent to about 20 percent by weight. The compound is most conveniently applied to the carrier by dissolving it in an inexpensive solvent and applying the solution to the sized clay in an appropriate solids mixer. The solvent is then typically removed by evaporation prior to application of the formulated granules to the soil.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The following examples provide an illustration of typical agriculturally-acceptable compositions comprehended by this invention.

| Wettable Powder | |
| --- | --- |
| Ingredient | Concentration by Weight (Percent) |
| N—[5-(1,1-Dimethylethyl)-6H-1,3,4-thiadiazin-2-yl]-2,6-dimethoxybenzamide | 50.0 |
| Igepal, a nonionic wetting agent, GAF Corporation | 5.0 |
| Polyfon O, lignosulfonate dispersant, Westvaco Corporation | 5.0 |
| Zeolex 7, a precipitated hydrated silica bulking agent, J. M. Huber Corporation | 5.0 |
| Barden Clay, a kaolinite clay, J. M. Huber Corporation | 35.0 |
| | 100.0 |

The ingredients are combined and finely ground to provide a free-flowing powder that can be suspended in water for convenient spray application.

| Aqueous Suspension | |
|---|---|
| Ingredient | Concentration by Weight (Percent) |
| N—[5-(1-Ethyl-1-methylpropyl)-6H-1,3,4-thiadiazin-2-yl]-2,6-dimethoxybenzamide | 45.0 |
| Polyfon H, an anionic lignosulfonate wetting agent and dispersant, Westvaco Corporation | 3.0 |
| Sponto 2174, an emulsifier, Witco Chemical Corporation | 4.0 |
| Ethylene Glycol | 8.0 |
| Xanthum Gum thickening agent | 0.2 |
| Antifoam C foam suppressant, Dow Corning Corporation | 0.5 |
| Water | 39.3 |
| | 100.0 |

The above ingredients are intimately admixed and finely ground to provide a suitable suspension, which is then further diluted with water at the application site.

| Dust | |
|---|---|
| Ingredient | Concentration by Weight (Percent) |
| N—[5-(1-Ethylcyclohexyl)-6H-1,3,4-thiadiazin-2-yl]-2,6-dimethoxybenzamide | 10.0 |
| Diatomite, a diatomaceous earth, Witco Chemical Corporation, Inorganic Specialties Division | 90.0 |
| | 100.0 |

The active ingredient and diatomaceous earth are intimately mixed and ground to a fine powder of uniform particle size of about 16 to about 40 microns. The dust thus formed may be applied by any number of conventional methods, for example by an aerial application.

| Granules | |
|---|---|
| Ingredient | Concentration by Weight (Percent) |
| N—[5-(1,1-diethylpropyl)-6H-1,3,4-thiadiazin-2-yl]-2,6-dimethoxybenzamide | 5.0 |
| Heavy aromatic naphtha | 5.0 |
| Bentonite 20/40 mesh granular clay, The Floridin Company | 90.0 |
| | 100.0 |

The compound is dissolved in the naphtha and sprayed onto the clay granules, typically under agitation, and the formulated granules are sieved to provide a uniform mesh size.

The herbicidal activity of representative compounds of the present invention is illustrated by the following experiment.

Experiment

The herbicidal activity of exemplary compounds of the present invention was evaluated at various application rates in a multiple species greenhouse test. Several weed and crop species were utilized to determine the herbicidal activity and selectivity of the test compounds. The compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied postemergence to some planted containers and preemergence to others using a DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence.

Table I presents preemergence herbicidal test results administered at 8 lbs/acre or less, while Table II presents postemergence test data administered only at 8 lbs/acre.

TABLE I

| | | Preemergence | | | | | | | | |
|---|---|---|---|---|---|---|---|---|---|---|
| Example No. of Compound Tested | Rate of Appln. lbs/acre | Crops | | | | | | | | |
| | | Corn | Cotton | Soybean | Wheat | Alfalfa | Sugar Beet | Rice | Cucumber | Tomato |
| 1 | 8.0 | 1 | | | | | | | | |
| | 4.0 | 1 | 1 | 1 | 1 | 1 | 1 | 1 | 1 | 3 |
| | 2.0 | 1 | 1 | 1 | 1 | 1 | 4 | 2 | 1 | 3 |
| | 1.0 | 1 | 1 | 1 | 1 | 1 | 1 | 1 | 1 | 1 |
| | 1.0 | 1 | 1 | 1 | 1 | 1 | 1 | 1 | 1 | 1 |
| | 0.5 | 1 | 1 | 1 | 1 | 1 | 1 | 1 | 1 | 1 |
| | 0.25 | 1 | 1 | 1 | 1 | 1 | 1 | 1 | 1 | 1 |

| | | Weeds | | | | | | | | | | |
|---|---|---|---|---|---|---|---|---|---|---|---|---|
| Example No. of Compound Tested | Rate of Appln. lbs/acre | Barnyard Grass | Lambs-quarter | Large Crab-grass | Mustard | Pig-weed | Foxtail | Wild Oat | Velvetleaf | Jimson-weed | Morning-glory | Zinnia |
| 1 | 8.0 | | | 1 | | 5 | 1 | | 1 | | 1 | 1 |
| | 4.0 | 1 | 5 | 1 | 4 | 4 | 2 | 1 | 1 | 4 | 1 | 1 |
| | 2.0 | 1 | 5 | 1 | 1 | 3 | 1 | 1 | 1 | 1 | 1 | 1 |
| | 1.0 | 1 | 5 | 1 | 3 | 5 | 1 | 1 | 1 | 1 | 1 | 1 |
| | 1.0 | 1 | 4 | 1 | 1 | 1 | 1 | 1 | 1 | 1 | 1 | 1 |

TABLE I-continued

| | Preemergence | | | | | | | | | | |
|---|---|---|---|---|---|---|---|---|---|---|---|
| 0.5 | 1 | 4 | 1 | 1 | 1 | 1 | 1 | 1 | 1 | 1 | 1 |
| 0.25 | 1 | 4 | 1 | 1 | 1 | 1 | 1 | 1 | 1 | 1 | 1 |

| Example No. of Compound Tested | Rate of Appln. lbs/acre | Crops | | | | | | | | |
|---|---|---|---|---|---|---|---|---|---|---|
| | | Corn | Cotton | Soybean | Wheat | Alfalfa | Sugar Beet | Rice | Cucumber | Tomato |
| 2 | 8.0 | | | | | | | | | 2 |
| | 4.0 | 2 | 2 | 4 | 4 | 4 | 4 | 4 | 4 | 5 |
| | 2.0 | 1 | 1 | 3 | 2 | 2 | 5 | 2 | 4 | 5 |
| | 1.0 | 1 | 1 | 2 | 1 | 1 | 2 | 1 | 1 | 2 |
| | 1.0 | 1 | 1 | 1 | | 2 | 3 | 1 | 1 | 2 |
| | 0.5 | 1 | 1 | 1 | 1 | 1 | 1 | 1 | 2 | 2 |
| | 0.25 | 1 | 1 | 1 | 1 | 1 | 1 | 1 | 1 | 1 |

| Example No. of Compound Tested | Rate of Appln. lbs/acre | Weeds | | | | | | | | | |
|---|---|---|---|---|---|---|---|---|---|---|---|
| | | Barnyard Grass | Lambs-quarter | Large Crab-grass | Mustard | Pig-weed | Foxtail | Wild Oat | Velvetleaf | Jimson-weed | Morning-glory | Zinnia |
| 2 | 8.0 | 4 | | 4 | 5 | 5 | 5 | 4 | 5 | | 5 | 4 |
| | 4.0 | 4 | 5 | 4 | 5 | 5 | 5 | 4 | 3 | 5 | 3 | 4 |
| | 2.0 | 4 | 5 | 4 | 5 | 5 | 4 | 3 | 2 | 4 | 4 | 2 |
| | 1.0 | 1 | 4 | 3 | 4 | 5 | 3 | 1 | 1 | 1 | 1 | 1 |
| | 1.0 | 1 | 4 | 4 | 3 | 3 | 2 | 1 | 1 | 3 | 3 | 2 |
| | 0.5 | 1 | 5 | 2 | 5 | 2 | 1 | 1 | 1 | 1 | 1 | 1 |
| | 0.25 | 1 | 5 | 2 | 1 | 3 | 1 | 1 | 1 | 2 | 1 | 1 |

TABLE II

| | | Postemergence | | | | | | | | | | |
|---|---|---|---|---|---|---|---|---|---|---|---|---|
| Example No. of Compound Tested | Rate of Appln. lbs/acre | Corn | Tomato | Large Crab-grass | Pigweed | Foxtail | Velvet-leaf | Morning-glory | Zinnia | Barnyard Grass | Mustard | Wildoat |
| 1 | 8.0 | 1 | | 1 | 1 | 1 | 1 | 1 | 1 | | | |
| 2 | 8.0 | | 3 | 1 | 2 | 2 | 1 | 2 | 2 | 2 | 3 | 1 |

I claim:

1. A compound of the formula

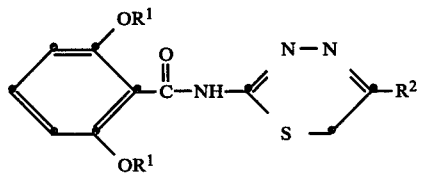

wherein:
each $R^1$ is independently methyl or ethyl;
$R^2$ is $C_1$–$C_{10}$ alkyl, $C_3$–$C_8$ cycloalkyl or $C_1$–$C_4$ alkyl substituted $C_3$–$C_8$ cycloalkyl; and the agronomically-acceptable salts thereof.

2. A compound of claim 1 wherein both $R^1$ substituents are methyl.

3. A compound of claim 2 wherein $R^2$ is $C_1$–$C_{10}$ alkyl.

4. The compound of claim 3 which is N-[5-(1,1-dimethylethyl)-6H-1,3,4-thiadiazin-2-yl]-2,6-dimethoxybenzamide.

5. The compound of claim 3 which is N-[5-(1-ethyl-1-methylpropyl)-6H-1,3,4-thiadiazin-2-yl]-2,6-dimethoxybenzamide.

6. A method for controlling undesired plants which comprises applying to the plants a growth inhibiting amount of a compound of claim 1.

7. A method of claim 6 wherein both $R^1$ substituents are methyl.

8. A method of claim 7 wherein $R^2$ is $C_1$–$C_{10}$ alkyl.

9. The method of claim 8 in which the compound is N-[5-(1,1-dimethylethyl)-6H-1,3,4-thiadiazin-2-yl]-2,6-dimethoxybenzamide.

10. The method of claim 8 in which the compound is N-[5-(1-ethyl-1-methylpropyl)-6H-1,3,4-thiadiazin-2-yl]-2,6-dimethoxybenzamide.

11. A herbicidal composition which comprises a growth inhibiting amount of a compound of claim 1 and an agriculturally-acceptable carrier.

12. A composition of claim 11 wherein both $R^1$ substituents are methyl.

13. A composition of claim 12 wherein $R^2$ is $C_1$–$C_{10}$ alkyl.

14. The composition of claim 13 in which the compound is N-[5-(1,1-dimethylethyl)-6H-1,3,4-thiadiazin-2-yl]-2,6-dimethoxybenzamide.

15. The composition of claim 13 in which the compound is N-[5-(1-ethyl-1-methylpropyl)-6H-1,3,4-thiadiazin-2-yl]-2,6-dimethoxybenzamide.

* * * * *